(12) United States Patent  
Barnett et al.

(10) Patent No.: US 8,128,131 B2  
(45) Date of Patent: Mar. 6, 2012

(54) FERRULE FOR MAKING FINGERTIGHT COLUMN CONNECTIONS IN GAS CHROMATOGRAPHY

(75) Inventors: Brett Russell Barnett, Ringwood (AU); Peter Alexander Dawes, Ringwood (AU)

(73) Assignee: SGE Analytical Science Pty Ltd, Ringwood, Victoria (AU)

( * ) Notice: Subject to any disclaimer, the term of this patent is extended or adjusted under 35 U.S.C. 154(b) by 142 days.

(21) Appl. No.: 12/471,815

(22) Filed: May 26, 2009

(65) Prior Publication Data

US 2010/0133806 A1 Jun. 3, 2010

(30) Foreign Application Priority Data

May 26, 2008 (AU) .................................. 2008902619

(51) Int. Cl.  
*F16L 17/00* (2006.01)

(52) U.S. Cl. ........................................ 285/339; 285/332

(58) Field of Classification Search .................. 285/339, 285/332.2, 332  
See application file for complete search history.

(56) References Cited

U.S. PATENT DOCUMENTS

| | | |
|---|---|---|
| 3,468,566 A | 9/1969 | Nietzel |
| 4,054,426 A | 10/1977 | White |
| 4,083,702 A | 4/1978 | Hartigan et al. |
| 4,293,415 A | 10/1981 | Bente et al. |
| 4,389,313 A | 6/1983 | Charney et al. |
| 4,669,756 A | 6/1987 | Cassaday et al. |
| 4,690,437 A | 9/1987 | Anderson |
| 4,713,963 A * | 12/1987 | Sharp ........................... 73/23.37 |
| 4,787,656 A | 11/1988 | Ryder |
| 4,792,396 A * | 12/1988 | Gundelfinger ............. 210/198.2 |
| 4,817,962 A | 4/1989 | Mott et al. |
| 4,991,883 A | 2/1991 | Worden |
| 5,163,215 A * | 11/1992 | Ledford, Jr. .................... 29/468 |
| 5,234,303 A | 8/1993 | Koyano |
| 5,288,113 A | 2/1994 | Silvis et al. |
| 5,938,919 A | 8/1999 | Najafabadi |
| 6,056,331 A | 5/2000 | Benett et al. |
| 6,193,286 B1 | 2/2001 | Jones et al. |
| 6,279,965 B1 | 8/2001 | Kida |

(Continued)

FOREIGN PATENT DOCUMENTS

WO 0173338 A1 10/2001

*Primary Examiner* — Aaron Dunwoody  
(74) *Attorney, Agent, or Firm* — Fulwider Patton LLP

(57) ABSTRACT

A ferrule arrangement for use in sealing connections to gas chromatography columns includes a generally tubular metal ferrule with an axial bore to receive a fracturable column with a protective coating. The ferrule has a forward part that tapers to a tip region of the ferrule. A generally tubular former has a socket portion to receive the ferrule and further has an internal conical surface that, after such receipt, engages the forward part of the ferrule. A portion is provided on either or both of said ferrule and the former by which the ferrule and former may be directly or indirectly relatively moved together by application of finger force. The taper and the internal conical surface exhibit relative taper angles and the tip region of the ferrule is sufficiently radially thin whereby the application of finger force (i) is adequate to move the ferrule axially into the former to cause the conical surface to engage the tip region of the ferrule and to deform the tip region into sealing engagement with the protective coating of the column, but (ii) does not break the column.

21 Claims, 4 Drawing Sheets

U.S. PATENT DOCUMENTS

| | | |
|---|---|---|
| 6,319,410 B1 | 11/2001 | Allington et al. |
| 7,316,777 B2 * | 1/2008 | Loy, Jr. .................. 210/198.2 |
| 7,507,336 B2 * | 3/2009 | Quimby et al. ............ 210/198.2 |
| 2006/0157983 A1 * | 7/2006 | Lyons et al. .................. 285/353 |
| 2010/0224546 A1 * | 9/2010 | Ellis et al. .................... 210/232 |

* cited by examiner

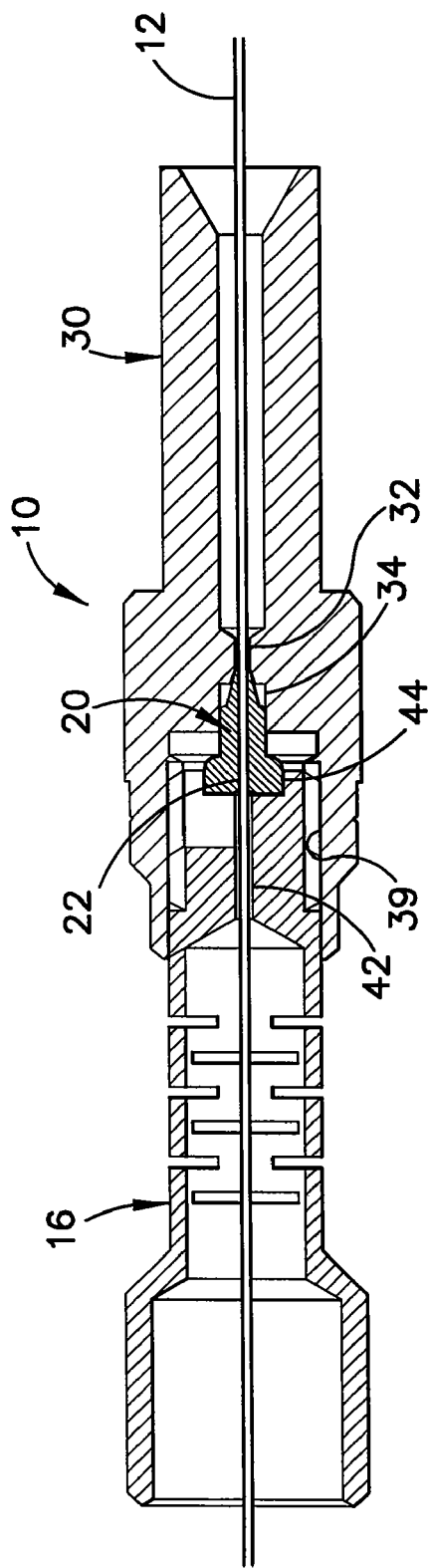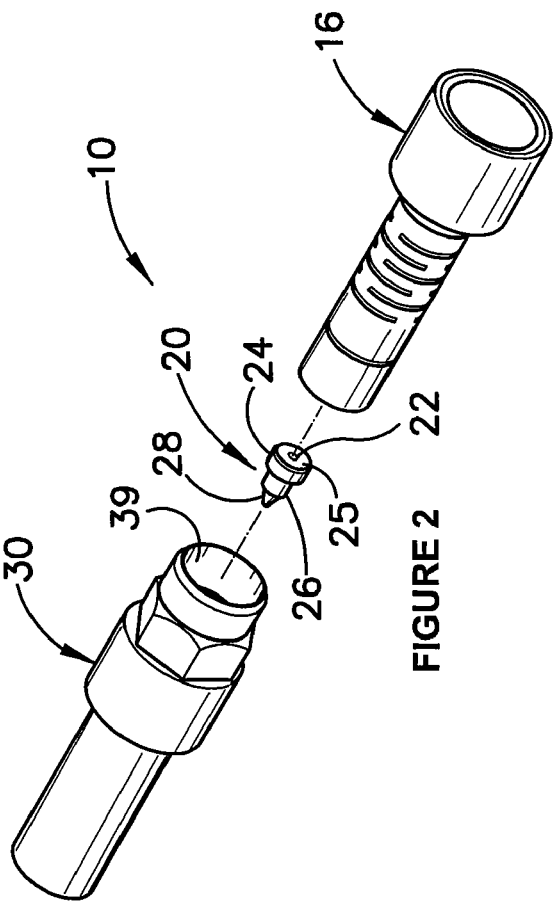

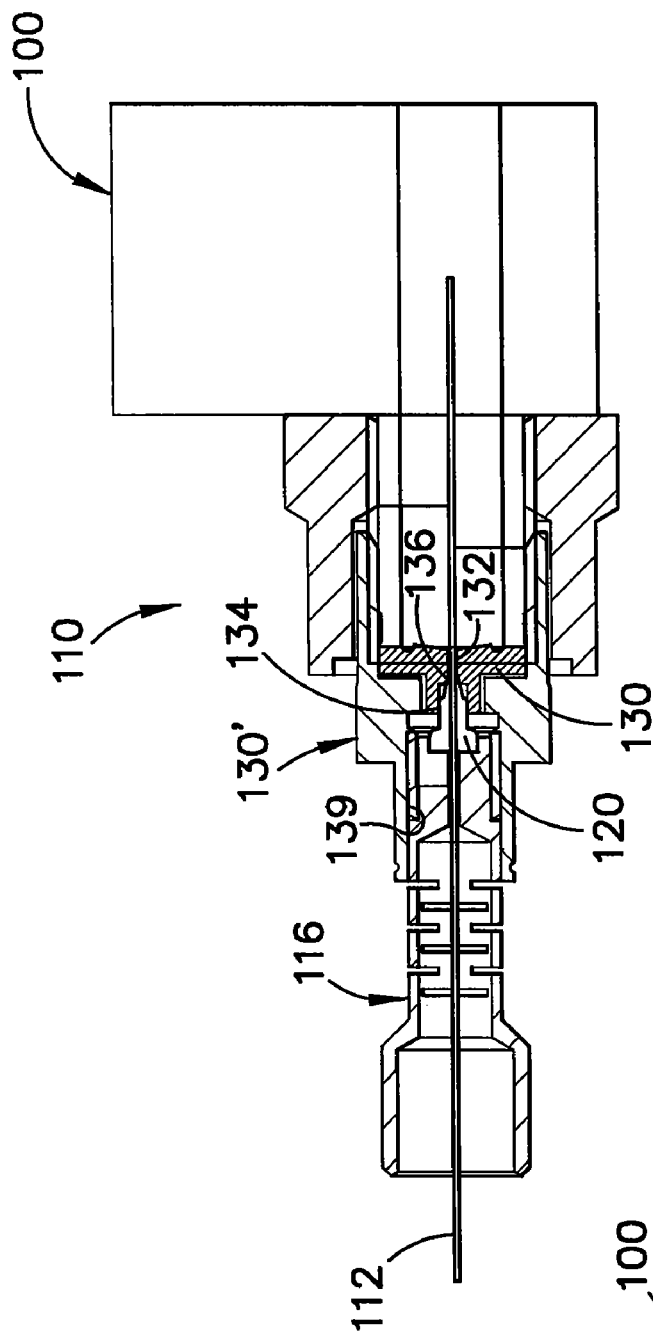
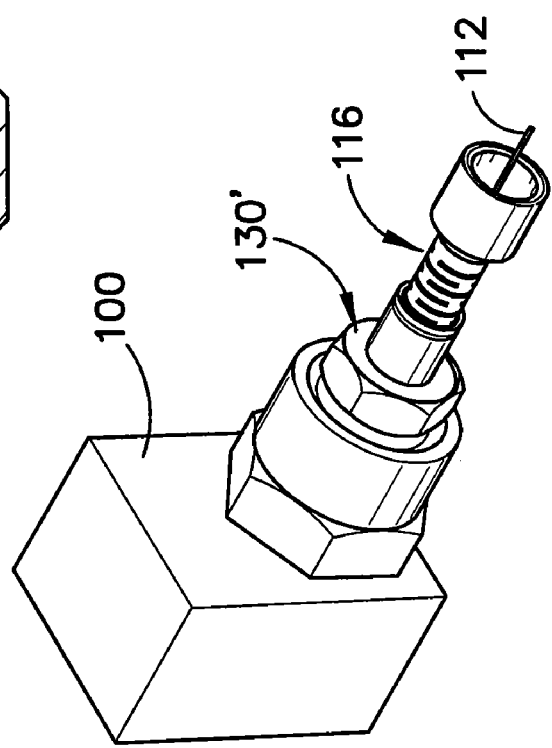
FIGURE 4
FIGURE 5

FERRULE FOR MAKING FINGERTIGHT COLUMN CONNECTIONS IN GAS CHROMATOGRAPHY

FIELD OF THE INVENTION

This invention relates generally to the sealing of fittings about fracturable tubes and as such is of particular, though not exclusive, interest in the sealing of connections to fused silica capillary columns in gas and liquid chromatography generally but more particularly in gas chromatography.

BACKGROUND OF THE INVENTION

In gas chromatography (GC) the sample to be analysed is introduced into the inlet end of a separation column and carried through the column by a carrier gas which is necessarily of high purity. To retain the sample to be analysed in the gas phase, it is usually necessary to heat the column to an elevated temperature. The inlet end of the column is usually above atmospheric pressure to allow the gas to be forced through the column. Consequently, the connection at the inlet end of the column needs to be gastight so as not to allow leakage from the column or introduce contamination into the column. The outlet end of the column can be connected to a number of devices, usually a detection device of some sort, and can also be the inlet of another column. The outlet end of the column may be at, below or above atmospheric pressure. The connection at the outlet end of the column will also be gastight to avoid introduction of contamination or leakage.

To seal the column at both inlet and outlet ends, conventional fittings employ ferrules that deform onto the outside of the column to make a substantially leaktight seal with the column as well as with the fitting, thereby forming a seal against the outside atmosphere.

Historically, when capillary columns were metal tubes, various types of ferrules were used including metal ferrules. Glass columns were introduced in the 1960s and immediately the all metal connection systems were unsuitable since they promptly broke the column. This was resolved by employing softer materials, notably silicon rubber, Teflon, graphite and, the most common, a Vespel (graphite polyimide) composite. The essential functional principle of the connection remained as before, but the seal was achieved without breaking the glass column.

Both graphite and the various types of polyimide ferrules had recognised deficiencies. Graphite ferrules were permeable to oxygen, which causes problems with detectors and damage to capillary columns. Furthermore graphite is an extremely absorptive material and will absorb sample constituents that are being analysed in the chromatographic system that it comes in contact with. The ferrule should not normally come in contact with sample components but it is recognised as a problem that pieces of graphite can become detached or extrude into parts of the chromatographic system thus destroying the integrity of the chromatographic separation. Whenever a capillary column was inserted through a graphite or polyimide ferrule to make a connection, a section of the column had to be cut off in case there were particles of ferrule material around the end of the column.

One of the main problems with polyimide and graphite-impregnated polyimide ferrules was that after an initial leaktight seal was made and the chromatographic system was heated, as is required in chromatographic analysis, and then the system cooled down in preparation for the next analysis, the polyimide ferrule developed substantial leaks necessitating the retightening of the fitting to re-establish the leaktight seal. On subsequent temperature cycles a leak might or might not develop. The thermal coefficients of expansion of polyimide materials were significantly higher than those of the metal components encapsulating them. This put the ferrule under significant compression at high temperatures causing it to creep dimensionally. As the fitting system was cooled, the polyimide ferrule contracted more than the metal fitting encapsulating it, which caused gaps and leakage paths to be formed.

In 1979, fused silica tubing was introduced. Fused silica is a high purity form of glass, which made it attractive for high accuracy, sensitive analysis. In addition this tubing could be produced with a much thinner wall thickness that allowed the tubing to be flexible in the same way as a fiber optic. This material is only strong and flexible without breaking when it is kept in the pristine state. Any damage from scratches (even from dust particles) or chemically from moisture in the environment causes the material to be highly brittle and structurally unstable so that it easily fractures. Like fiber optics, this issue was addressed by supplying the fused silica tubing with a fine protective coating that in the vast majority of products was a polyimide coating of thickness typically in the range 5 to 100 micron.

The connection systems used for these gas chromatography fused silica columns continued to be the systems carried over from the glass columns that preceded the fused silica columns, that is systems containing ferrules made of graphite or graphite polyimide composite. The aforementioned problems arising from reliance on such ferrules remained and were reluctantly tolerated and compensated for, accepted as the "downside" price of employing columns that were themselves a very satisfactory vehicle for the gas chromatography technique.

For many years, these various deficiencies of existing graphite and polyimide ferrule systems diminished the reliability of chromatography systems, leading to compromised performance as well as non-productive time in rectifying the faults. In addition, damage to components in the systems regularly occurred when operators applied excessive force to fittings in efforts to eliminate leaks.

International patent publication WO 01/73338 disclosed the concept that, in contrast to longstanding wisdom, metal ferrules could be employed to seal connections to fused silica capillary columns because it was possible to make an effective seal at the interface between the metal ferrule and the polyimide coating on the column without fracturing the underlying glass. It was realised that the coating, fine as it was, made the use of metal ferrules feasible.

The structure disclosed in WO 01/73338, and the actual product brought to market by the assignee, did continue to share one disadvantage with the predecessor arrangements that relied on graphite or polyimide ferrules: in gas chromatography, a tool such as a wrench or spanner lever was necessary to reliably deliver the necessary compression force. The spanner tightening approach has also been accepted as part of what is required to connect thin wall fused silica tubing into a gas chromatography system despite the problems caused by practitioners overtightening fittings, including damage to threads and separation columns and breaking of expensive fittings in the system.

In contrast, fitting systems used in liquid chromatography (LC) can be tightened with just the application of finger force but these have very different requirements in terms of the level of leak tightness and high temperature needs, and they are not sealing directly onto thin wall fracturable glass. Liquid chromatography systems rely on polymer materials like PEEK which has a low enough modulus that sufficient force can be generated to adequately deform the ferrule without the leverage of a spanner. These fingertight fittings are the standard approach in LC. The reason that these have never been used in gas chromatography is the requirement for high temperature operation and sealing of very non-viscous and potentially hazardous gases like hydrogen. There have been a number of attempts over the last 20 years to commercialise simplified GC connector systems that did not require spanners but none have been successful.

An object of the invention is a ferrule and fitting design that allows fused silica tubing to be sealed into a gas chromatography system by finger force alone, i.e. without recourse to spanners or like tools and using the force applied by the fingers (including the thumb) alone without use of leverage or force from the wrist, elbow or shoulder.

SUMMARY OF THE INVENTION

In one aspect, the invention provides a ferrule arrangement for use in sealing connections to gas chromatography columns, that includes a generally tubular metal ferrule with an axial bore to receive a fracturable column with a protective coating. The ferrule has a forward part that tapers to a tip region of the ferrule. A generally tubular former has a socket portion to receive the ferrule and further has an internal conical surface that, after such receipt, engages the forward part of the ferrule. A portion is provided on either or both of the ferrule and the former by which the ferrule and former may be directly or indirectly relatively moved together by application of finger force. The taper and said internal conical surface exhibit relative taper angles and said tip region of the ferrule is sufficiently radially thin whereby the application of finger force (i) is adequate to move the ferrule axially into the former to cause the conical surface to engage the tip region of the ferrule and to deform the tip region into sealing engagement with the protective coating of the column, but (ii) does not break the column.

Said portion may be a face engageable by a finger rotatable connector component. The arrangement may further include a connection component rotatable by finger force to relatively move the ferrule and former together. This connector component may be one component of a connector assembly, and the former another component of the connector assembly, which components are threadingly engageable together.

In an embodiment of the ferrule arrangement, the rearward part of the ferrule is an intermediate part, and there is a more rearward part of external diameter greater than the intermediate part and the forward part. This more rearward part may form a finger engageable portion, and may be knurled to optimise the grip of fingers grasping it.

In an embodiment, the rearward part of the ferrule and the socket portion of the former have co-operatively engageable threads for drawing the female into the former by relative mutual rotation.

The former preferably has an axially extending bore with a counterbore that provides said socket, and with the internal conical surface formed in the bore immediately adjacent the inner end of the counterbore. The bore of the former is preferably of greater diameter than the bore of the ferrule so that the tip of the ferrule projects into the bore of the former, the internal conical surface engages the tip region behind the actual tip.

The former is preferably also metal, and the preferred metal for both the ferrule and the former is stainless steel.

In its first aspect, the invention extends to the ferrule arrangement as an assembly of the ferrule and the former.

In another aspect, the invention provides a ferrule for use in sealing connections to gas chromatography columns, comprising a generally tubular metal body with an axial bore to receive a fracturable column with a protective coating, which ferrule has a rearward part of larger outer diameter and an intermediate part of lesser outer diameter than the rearward part, and a forward part of outer diameter less than the rearward and intermediate parts that tapers to a tip region of said ferrule that is deformable into sealing engagement with the protective coating of the capillary column on being deformed by a former surface against which the ferrule is pushed by direct or indirect finger movement of the rearward part.

In both aspects, the radial thickness of the tip region of the ferrule at the tip thereof is preferably between 0.05 and 0.15 mm, more preferably in the range 0.5 and 0.15 mm. The forward part of the ferrule is preferably uniformly tapered. From the wider rearward end of the taper to the tip of the ferrule, the radial thickness advantageously diminishes by 75% or more. The axial length of the taper is similar in dimension to its external diameter as its wider end.

BRIEF DESCRIPTION OF THE DRAWINGS

The invention will now be further described, by way of example only, with reference to the accompanying drawings, in which:

FIG. 1 is an axial cross section of a connection assembly at the inlet end of a fused silica chromatography column, incorporating a ferrule arrangement according to a preferred embodiment of the invention;

FIG. 2 is a fragmentary isometric view of the connection assembly depicted in FIG. 1;

FIG. 4 is a view similar to FIG. 1 of a connection assembly at the outlet end of a fused silica chromatography column, for example to a detector or analyser instrument; and FIG. 5 is an isometric view of the connection assembly depicted in FIG. 4.

DETAILED DESCRIPTION OF EMBODIMENTS OF THE INVENTION

Figure 3:
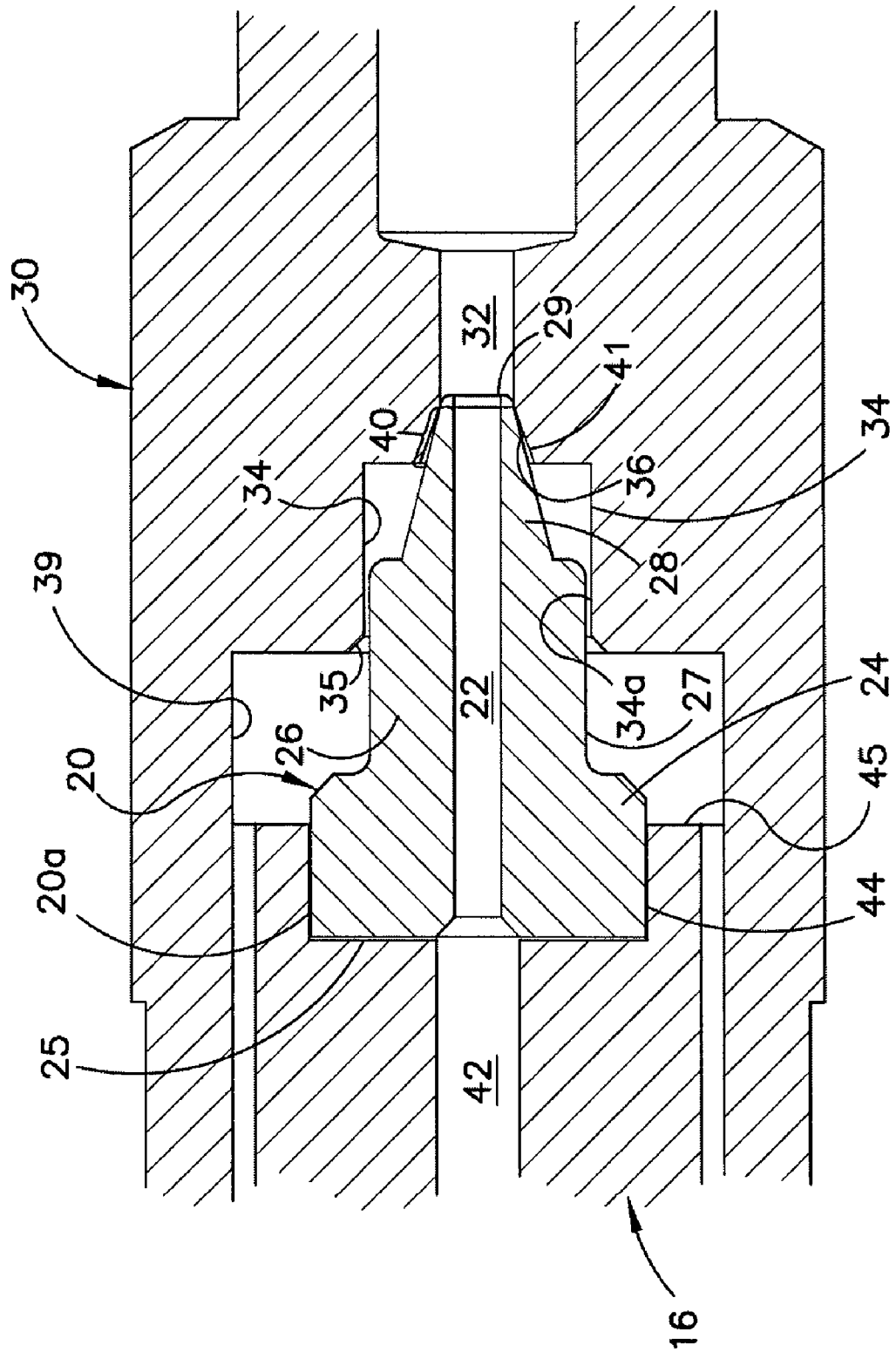
FIG. 3 is an enlargement of part of FIG. 1, better depicting the ferrule and adjacent components but omitting the fused silica column.
Figure 3A:
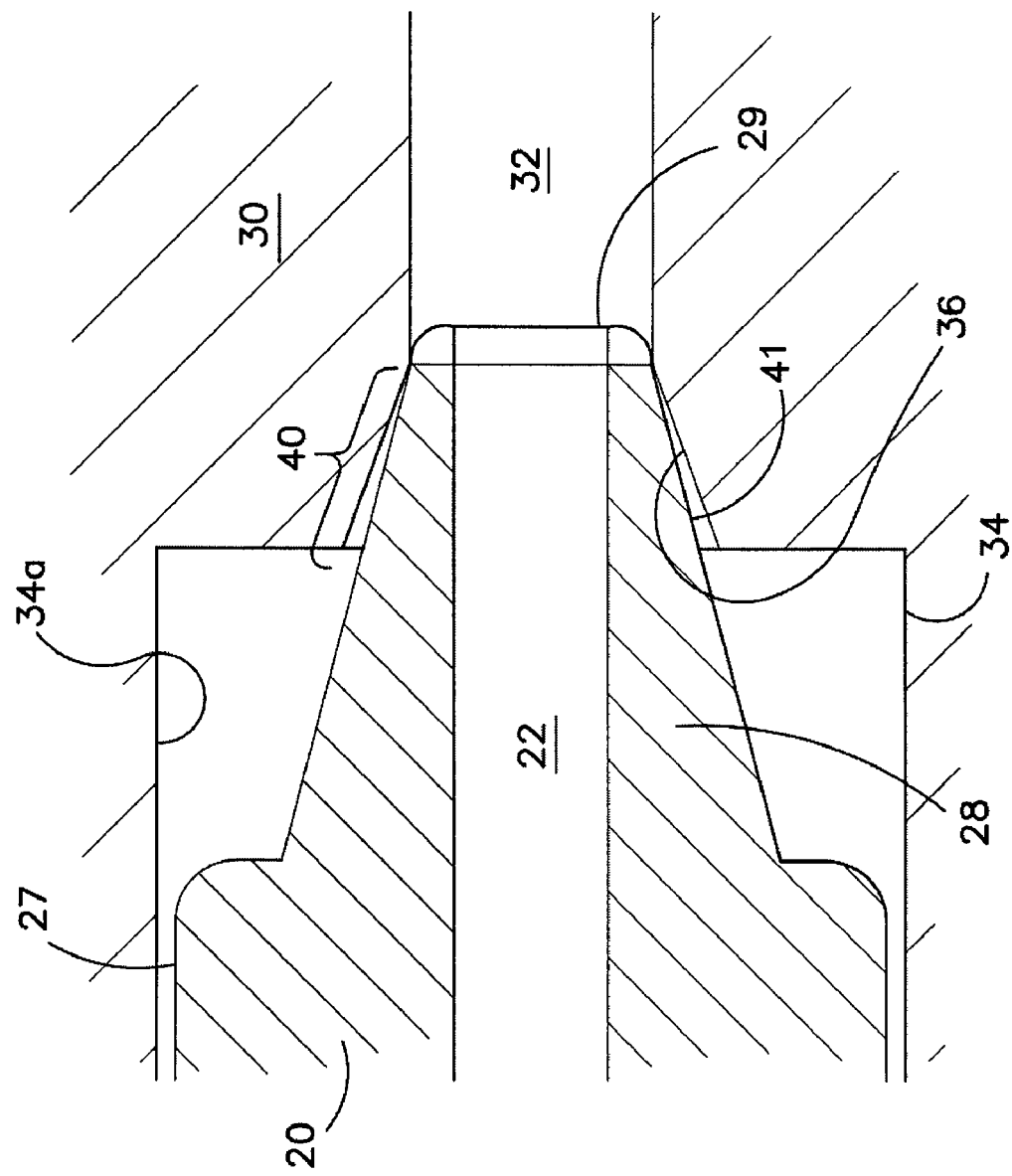
FIG. 3a is a further enlargement of part of FIG. 3.

FIG. 1 illustrated a typical connection assembly 10 at an inlet end of a fused silica column 12. The assembly includes a generally tubular female column connector 30, a complementary male column connector 16, and, centrally seated in respective co-axial counterbores 34, 44, a ferrule 20. Male and female connectors 16, 30 are threadingly engaged at internal interface 39 for relative axial movement by relative finger rotation of the two components.

Ferrule column connector 30 serves as former for ferrule 20. All three components are preferably formed in stainless steel and all have a central bore 22, 32, 42 to receive a fused silica glass tube 12, which is of the kind commonly employed as a column in gas chromatography. This tube 12 may generally be of outside diameter 0.3 to 1.0 mm and typically has a protective polyimide coating of thickness around 15 micron, although it may be in the range 5 to 100 micron. Other coatings are also known, including silicone and, for specialist applications, a metal such as aluminium.

The fused silica tube 12 is typically a close but adjustable fit within the ferrule bore 22, for example a nominal bore of 0.4 mm for standard fused silica tube of outside diameter 0.36 mm. The bore 32 of the former is somewhat larger, for reasons to be explained: for the standard tube of outside diameter 0.36 mm, the bore 32 of the former 30 is preferably about 0.65 mm.

Ferrule 20 is an axially symmetrical one-piece stainless steel component in three principal parts. With reference to FIG. 3, an intermediate part 26 has an outer cylindrical surface 27 of intermediate diameter between a rearward terminal part 24 of greater diameter than intermediate part 26, and a forward part 28 of smaller outer diameter. Rearward terminal part 24 defines a flat rear end face 25 of the ferrule, and seats snugly in counterbore 44 in the endface 45 of make connector 16. Forward part 28 projects axially from intermediate part 26 and tapers uniformly to a flat faced tip 29 terminating a tip region 40. The tapered surface of the tip region 40 is indicated at 41.

At its rear, former 30 has, in addition to axially extending bore 32, a larger counterbore 39 that receives make connector 16, and, at the inner end of counterbore 39, an axially symmetrical counterbore 34. The internal cylindrical surface 34a of counterbore 34 provides a close-fitting sliding socket for intermediate part 26 of ferrule 20. The open mouth of counterbore 34 is chamfered at 35. A portion of former bore 32 immediately adjacent counterbore 34 is outwardly flared to form an internal conical surface 36.

On finger-operated rotational tightening of male connector 16, intermediate part 26 of the ferrule 20 is pushed into counterbore socket 34 of the former and eventually the tip 29 extends past the inner end of internal conical surface 36 into bore 32. Shortly after, the tapered surface 41 of tip region 40 engages internal conical surface 36: the tapered part 28 has been so designed that further finger rotation of male column connector 16 will result in inward deformation of the tapered tip region 40 into sealing engagement with the protective coating of the fused silica column 12. Indeed, the tip region 40 is sufficiently radially thin that application of finger force to male connector 16 is (i) adequate to relatively move the ferrule axially into the former to cause the internal conical surface 36 to engage the tip region 40 of the ferrule and to deform the tip region into sealing engagement with the protective coating of the column. On the other hand, the tip region 40 of the ferrule and the internal conical surface 36 of the former are such that this application of finger force is incapable of fracturing the column.

The conical surface 36 and the tapered surface 41 preferably have different taper angles: surface 41 is typically at a shallower angle than surface 36 to limit the size of the sealing area and to reduce the force required to deform. In general the resultant thin line sealing is more effective. By way of example, the included angle of tapered surface 41 of ferrule tip region 40 is about 30°, and the included angle of internal conical surface 36 is about 40°, a difference of about 10° (i.e., a relative taper angle of 5° between the actual surfaces). The included angle of tapered surface 41 may be in the range between 20° and 60° but is preferably in the range 25-35°. The included angle of internal conical surface 36 may be in the range 25-70° but is preferably in the range 35-45°. The angle difference between the two included angles is therefore preferably greater than 0° up to 20°, and the relative taper angle is greater than 0° up to 10°.

It will be appreciated that the protective (polyimide) coating of the fused silica column provides a medium that may be deformed by the inwardly deflected tip region of the ferrule to achieve an adequate seal for gas chromatography but without finger force being able to so deform the tip region as to breach the protective coating and fracture the glass.

Preferred features by which this outcome is achieved include one or more of the following:
(i) The radial thickness of the tip region of the ferrule at the tip thereof is between 0.05 and 0.15 mm, preferably in the range 0.5 to 0.15 mm.
(ii) The tapered surface 41 of the ferrule is uniformly tapered.
(iii) From the wider rearward end of the taper 41 to the tip 29 of the ferrule, the radial thickness about bore 22 diminishes by 75% or more.
(iv) The axial length of the taper 41 is similar in dimension to its external diameter at its wider end.

FIG. 4 is a similar view to FIG. 1 of a connection assembly 110 at the inlet end of column 112 to a detector or analyser instrument 100. Corresponding parts are indicated by like reference numerals preceded by a "1": in this case the male column connector 116 is similar in form to male column connector 16 of the first embodiment, while the female column connector 130' and former 130 are separate components: former 130 is a flanged disk designed to suit the instrument port, but still provided with a bore 132 to receive column 112, counterbore 134 to seat ferrule 120 and internal conical surface 136.

In the illustrated applications, the finger force is applied indirectly to the components. Alternatively, the outermost cylindrical surface 20a of ferrule 20 may have knurling or other features to facilitate finger rotation, and the outer surface 27 of intermediate part 26 may be threaded to co-operatively engage a corresponding thread on counterbore socket 34 of former 30. This will permit use of direct finger force to effect relative rotation of the parts to form a fingertight sealed connection.

It is preferable that friction between the ferrule and former components is minimal so that the engaging surfaces are able to relatively slide over each other, and so that the fitting can easily be undone. Although gauling of the ferrule and threads is found to be not a major issue, it can be further avoided or minimised if necessary by silver plating of the ferrule, former and other relevant parts or by applying a coating of a smooth formed anti-friction medium such as molybdenum disulphide. Such a coating may be as little as 1 micron thick.

We claim:
1. A ferrule arrangement for use in sealing connections to gas chromatography columns, comprising:
   a generally tubular metal ferrule with a continuous smooth axial bore to receive a fracturable column with a protective coating, which ferrule has a forward part that tapers to a tip region of said ferrule;
   a generally tubular former having an axially extending bore with a counterbore that provides a socket portion to receive said ferrule and further having an internal conical surface that, after such receipt, engages said forward part of the ferrule, said internal conical surface formed in the bore immediately adjacent an inner end of the counterbore; and
   a portion on either or both of said ferrule and said former by which the ferrule and former may be moved together by application of finger force alone;
   wherein said taper and said internal conical surface exhibit relative taper angles and said tip region of said ferrule is sufficiently radially thin whereby said application of finger force alone (i) is adequate to move the ferrule axially into the former to cause said conical surface to engage the tip region of the ferrule and to deform the tip region into sealing engagement with said protective coating of the column, but (ii) does not break the column; and wherein the bore of the former is of greater diameter than the bore of the ferrule and the tip region of the ferrule at the tip thereof has a radial thickness between 0.05 and 0.15 mm so that the tip of the ferrule projects into the bore of the former and beyond said internal conical surface, and said internal conical surface engages the tip region behind the actual tip of the ferrule.

2. A ferrule arrangement according to claim 1 wherein said portion on either or both of said ferrule and said former by which the ferrule and former may be moved together by application of finger force alone is a face engageable by a finger rotatable connector component.

3. A ferrule arrangement according to claim 2 further including a connector component rotatable by finger force to relatively move said ferrule and former together.

4. A ferrule arrangement according to claim 3 wherein said connector component is one component of a connector assembly, and said former is another component of the connector assembly, which components are threadingly engageable together.

5. A ferrule arrangement according to claim 4 wherein the former is also metal.

6. A ferrule arrangement according to claim 5 wherein the ferrule and former are both bodies of stainless steel.

7. A ferrule arrangement according to claim 4 wherein a rearward part of the ferrule is an intermediate part, and there is a more rearward part of external diameter greater than the intermediate part and the forward part.

8. A ferrule arrangement according to claim 1 wherein the former has an axially extending bore with a counterbore that provides said socket, and with the internal conical surface formed in the bore immediately adjacent the inner end of the counterbore.

9. A ferrule arrangement according to claim 1 wherein the former is also metal.

10. A ferrule arrangement according to claim 9 wherein the ferrule and former are both bodies of stainless steel.

11. A ferrule arrangement according to claim 1 comprising an assembly of the ferrule and the former.

12. A ferrule arrangement according to claim 1 wherein said relative taper angle is greater than 0° up to 10°.

13. A ferrule arrangement according to claim 12 wherein the included angle of said taper is in the range 25-35°.

14. A ferrule arrangement according to claim 12 wherein the included angle of the internal conical surface is in the range 35-45°.

15. A ferrule arrangement according to claim 12 wherein the radial thickness of the tip region of the ferrule at the tip thereof is in the range 0.5 to 0.15 mm.

16. A ferrule arrangement according to claim 1 wherein the radial thickness of the tip region of the ferrule at the tip thereof is in the range 0.5 to 0.15 mm.

17. A ferrule arrangement according claim 1 wherein the forward part of the ferrule is uniformly tapered.

18. A ferrule arrangement according to claim 1 wherein, from a wider rearward end of the taper to the tip of the ferrule, the radial thickness diminishes by 75% or more.

19. A ferrule arrangement according to claim 1 wherein a rearward part of the ferrule is an intermediate part, and there is a more rearward part of external diameter greater than the intermediate part and the forward part.

20. An assembly comprising:
a ferrule arrangement according to claim 1; and
a fracturable column with a protective coating received by said bore of the ferrule.

21. An assembly according to claim 20 wherein the fracturable column is a fused silica tube and the protective coating is polyimide.

\* \* \* \* \*